United States Patent
Mohapatra et al.

(10) Patent No.: US 9,550,992 B2
(45) Date of Patent: Jan. 24, 2017

(54) COMPOSITIONS AND METHODS FOR MODULATING MYELOID DERIVED SUPPRESSOR CELLS

(71) Applicants: UNIVERSITY OF SOUTH FLORIDA, Tampa, FL (US); Shyam S. Mohapatra, Lutz, FL (US); Srinivas Nagaraj Bharadwaj, Tampa, FL (US); Subhra Mohapatra, Lutz, FL (US)

(72) Inventors: Shyam S. Mohapatra, Lutz, FL (US); Srinivas Nagaraj Bharadwaj, Tampa, FL (US); Subhra Mohapatra, Lutz, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/361,537

(22) PCT Filed: Dec. 3, 2012

(86) PCT No.: PCT/US2012/067586
§ 371 (c)(1),
(2) Date: May 29, 2014

(87) PCT Pub. No.: WO2013/082591
PCT Pub. Date: Jun. 6, 2013

(65) Prior Publication Data
US 2014/0336239 A1 Nov. 13, 2014

Related U.S. Application Data

(60) Provisional application No. 61/566,158, filed on Dec. 2, 2011.

(51) Int. Cl.
| | | |
|---|---|---|
| *C12N 15/11* | (2006.01) | |
| *C12N 15/113* | (2010.01) | |
| *C12Q 1/68* | (2006.01) | |
| *C12N 5/0789* | (2010.01) | |
| *C12N 5/0784* | (2010.01) | |
| *C12N 5/0786* | (2010.01) | |

(52) U.S. Cl.
CPC .......... *C12N 15/113* (2013.01); *C12N 5/0639* (2013.01); *C12N 5/0645* (2013.01); *C12N 5/0647* (2013.01); *C12N 15/111* (2013.01); *C12Q 1/6883* (2013.01); *C12N 2310/141* (2013.01); *C12N 2310/17* (2013.01); *C12N 2320/30* (2013.01); *C12N 2501/65* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2011/0059106 A1 3/2011 Kuchroo

FOREIGN PATENT DOCUMENTS

CN 101804207 A * 8/2010

OTHER PUBLICATIONS

Liu et al., MiR-223 suppresses differentiation of tumor-induced CDIIb+Gr1+ myeloid-derived suppressor cells from bone marrow cells International Journal of Cancer, Jan. 6, 2011, vol. 129, Issue 11, pp. 2662-2673 See abstract and pp. 2666-2667.
Corzo et al., 'HIF-1alpha regulates function and differentiation of myeloid-derived suppressor cells in the tumor microenvironment'The Journal of Experimental Medicine, Oct. 25, 2010, vol. 207, No. 11, pp. 2439-2453 See abstract; figure 6; and pp. 2446-2448.
Shina et al., 'Prostaglandin E2 promotes tumor progression by inducing myeloid-derived suppressor cells' Cancer research, May 4, 2007, vol. 67, No. 9, pp. 4507-4513 See abstract; figure 2; and pp. 4508-4509.
Condamine et al., 'Molecular mechanisms regulating myeloid-derived suppressor cell differentiation and function' Trends in Immunology, Jan. 2011, vol. 32, Issue 1, pp. 19-25 See abstract.
Ostrand-Rosenberg et a l . , 'Myeloid-derived suppressor cells: linking inflammation and cancer' The Journal of Immunology, Apr. 15, 2009, vol. 182, No. 8, pp. 4499-4506 See pp. 4502-4503.
Nelson et a l . , 'Role of myeloid derived syppressor cells in asthma' WAO Journal, Feb. 2012, p. S26. See the whole document.
International Search Report and Written Opinion, dated Mar. 15, 2013.
Zhang, et al., "Both miR-17-5p and miR-20a Alleviate Suppressive Potential of Myeloid-Derived Suppressor Cells by Modulating STAT3 Expression", Journal of Immunology, Mar. 7, 2011.
Tilil, et al., "Expression and function of micro RNAs in immune cells during normal or disease state", International Journal of Medical Sciences, 2008 5(2): 73-79.
Aimee Jackson, "The Therapeutic Potential of microRNA Modulation", Discovery Medicine, Apr. 10, 2010.

* cited by examiner

*Primary Examiner* — Kate Poliakova-Georgantas
(74) *Attorney, Agent, or Firm* — Thomas | Horstemeyer, LLP

(57) ABSTRACT

Provided are methods and compositions for modulating the differentiation of a myeloid derived suppressor cell (MDSC). In particular, described herein are miR-142 polynucleotides and miR-223 polynucleotides that can be used to modulate differentiation of MDSCs. Increased differentiation of a MDSC population, or cells within an MDSC population, can be achieved by increasing the miR-142 and/or miR-223 polynucleotides in a MDSC.

16 Claims, 16 Drawing Sheets

Control                Allergic Mice

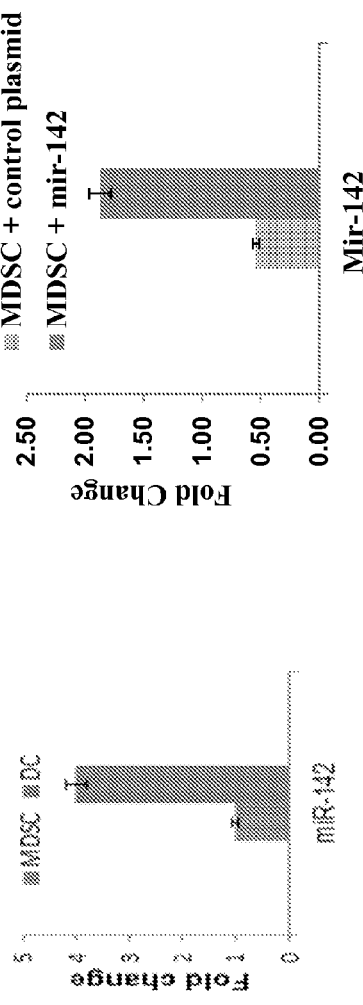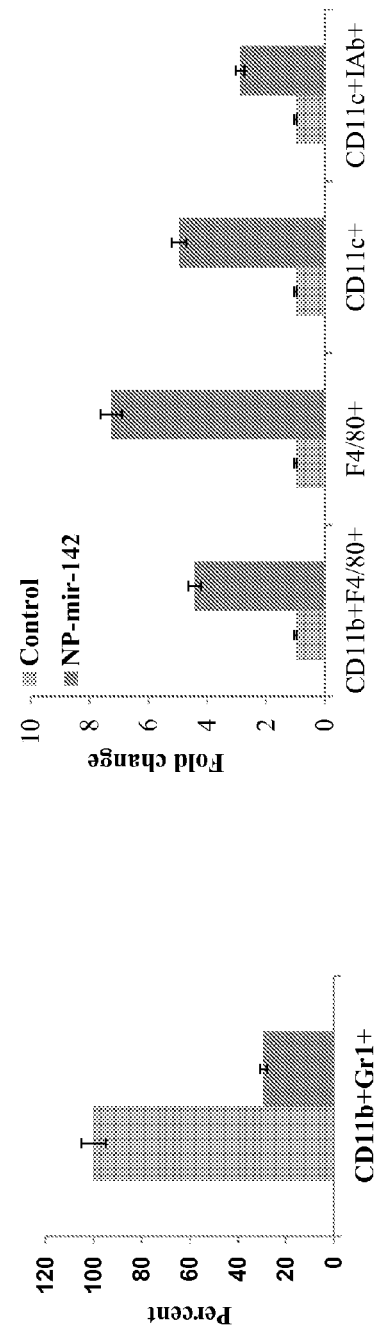
FIG. 5A FIG. 5B FIG. 5C FIG. 5D

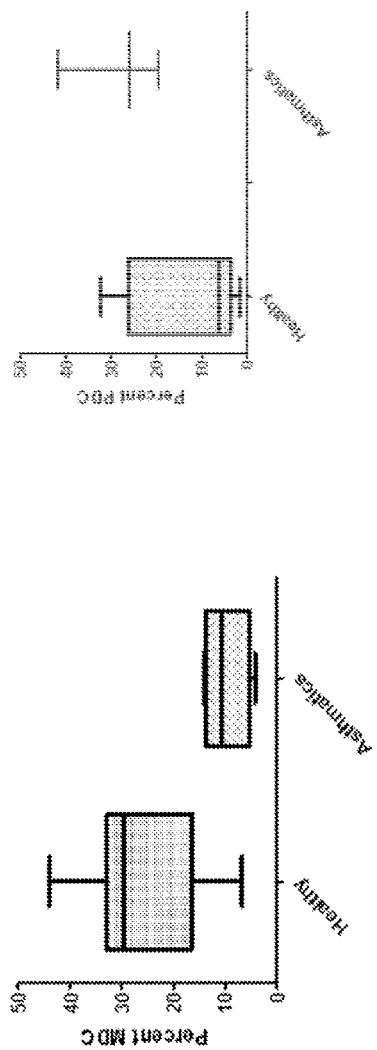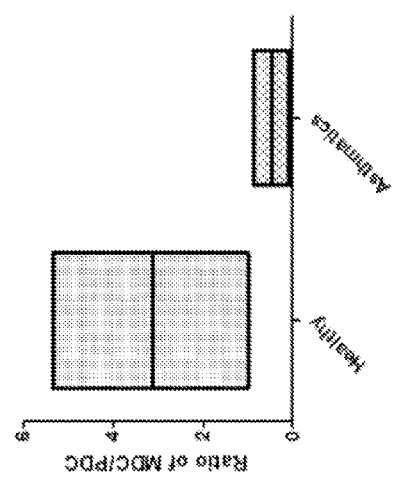

COMPOSITIONS AND METHODS FOR MODULATING MYELOID DERIVED SUPPRESSOR CELLS

CROSS-REFERENCE TO RELATED APPLICATION

This application is the 35 U.S.C. §371 national stage of, and claims priority to and the benefit of, PCT application PCT/US2012/067586, filed Dec. 3, 2012, which claims priority to and the benefit of U.S. Provisional Application No. 61/566,158, filed on Dec. 2, 2011, herein incorporated by reference in its entirety.

STATEMENT REGARDING FEDERALLY SPONSORED RESEARCH OR DEVELOPMENT

This invention was made with government support 1P30HL101265-01awarded by the National Institutes of Health. The Government has certain rights to the invention.

BACKGROUND

Myeloid derived suppressor cells (MDSCs) are comprised of a mixture of immature myeloid cells such as granulocytes and monocyte-macrophages as well as myeloid cell precursors at various stages of differentiation. MDSCs are also known as immature myeloid cells, or IMCs. MDSCs were originally categorized as suppressor cells due to their ability to suppress the activation of T cells. It is believed that MDSCs function in part to protect the host from the harmful effects of excessive immune stimulation during acute and chronic infections, and to the limit the generation of autoimmune responses towards tissue antigens released by trauma.

MDSCs in mice are characterized as $CD11b^+Gr-1^+$ (Nagaraj, S., et al. Nat Med 13, 828-835 (2007); Nagaraj, S., Schrum, A. G., Cho, H. I., Celis, E. & Gabrilovich, D. I. J Immunol 184, 3106-3116 (2010); Nagaraj, S. & Gabrilovich, D. I. Cancer J 16, 348-353 (2010); Herber, D. L., et al. Nat Med 16, 880-886 (2010); Ramakrishnan, R., et al. J Clin Invest 120, 1111-1124 (2010)). The myeloid lineage differentiation antigen Gr-1 (Ly6G and Ly6C) is expressed on myeloid precursor cells, granulocytes, and transiently on monocytes (Youn, J. I., Nagaraj, S., Collazo, M. & Gabrilovich, D. I. J Immunol 181, 5791-5802 (2008)). The CD11b receptor (Mac-1) is an integrin that is expressed on the surface of monocytes/macrophages, dendritic cells (DC), granulocytes, and activated B- and T-lymphocytes. $Gr-1^{++}CD11b^+$ cells represent 30-40% of normal bone marrow cells and 2-4% of all nucleated normal splenocytes. In humans, MDSCs are characterized in humans as $Lin_-$ $HLADR^-CD33^{+}$. CD33 is also referred to as siglec-3. There may be different subsets of MDSCs as evidenced by heterogeneous expression of CD14 and CD15 in MDSC populations.

Although the action MDSCs may be beneficial in dampening certain autoimmune responses, the proliferation of MDSCs is associated with activation of these cells in a pathological context. Activation is mediated through several transcription factors and results in the up regulation and expression of immunosuppressive factors such as ARG1 and NOS2, up regulation of activity of the NADPH oxidase complex, and an increase in the production of NO, ROS, RNS, and cytokines. During chronic inflammation in particular, the accumulation of MDSC leads to a sustained immunosuppressive environment that inhibits the process of differentiation/maturation (Nagaraj, S., et al. Nat Med 13, 828-835 (2007); Movahedi, K., et al. Blood 111, 4233-4244 (2008); Nagaraj, S., et al. Nat Med 13, 828-835 (2007); Kusmartsev, S., Nefedova, Y., Yoder, D. & Gabrilovich, D. I. J Immunol 172, 989-999 (2004)). The inability of the host system to mount an effective immune response is one of the major factors responsible for tissue injury in chronic inflammation. MDSCs also play one of the major roles in tumor associated immune abnormalities and other infections.

WT or Tg mice BM cells were cultured with LPS 50 ng/ml for 5 days. Bar graph denotes fold difference of MDSC analyzed by flow cytometer.

FIG. 5 illustrates that overexpression of miR-142 induces MDSC differentiation. (A) BM-derived cells were cultured with LPS (to derive MDSC), and with GM-CSF and IL-4 to derive DCs. On day 7, MDSCs and DCs were examined for miR-142. Bars represent expression of miR-142 as relative fold change over control MDSC. (B-D) MDSC were isolated at a purity of 96% from chronic inflamed mice. MDSCs were transfected with chitosan-pmir142 or control plasmid and cultured for 5 days. DCs, macrophages and MDSCs were analyzed using flow cytometry on day 3 and 5 (not shown). Bars denote (B) Mir-142 expression in MDSCs, (C) CD11bGr1 (MDSC) in culture, and (D) fold changes of DCs and macrophages.

Figure 6:
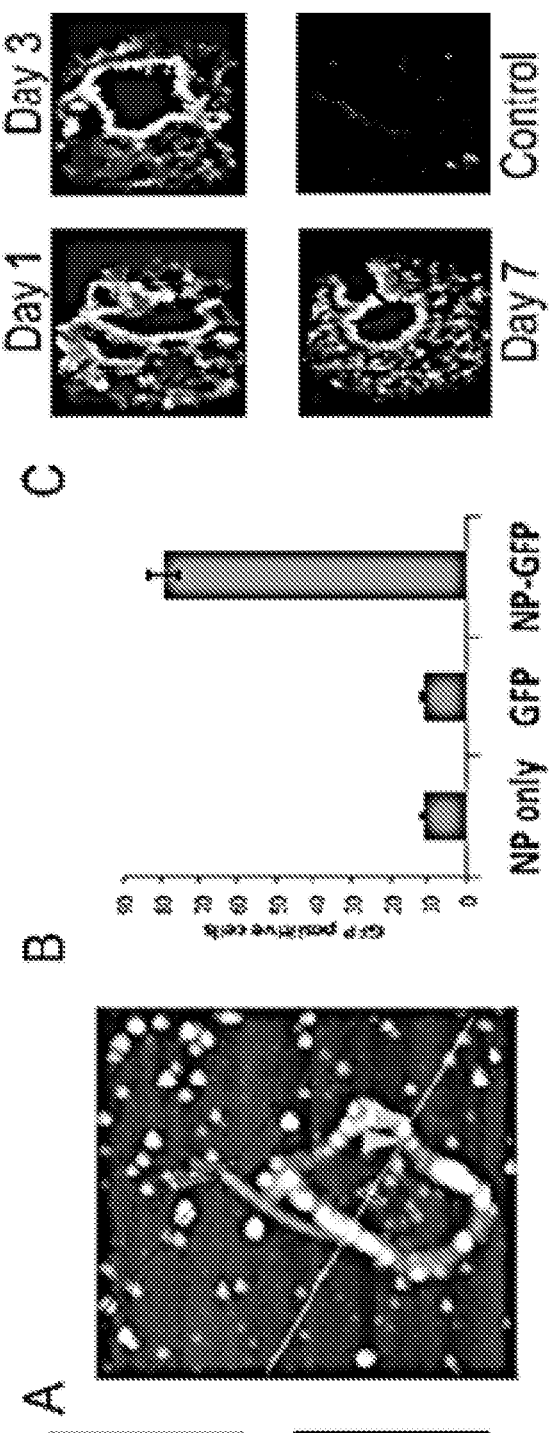

FIG. 6(A-C) illustrates the development and characterization of the miR-142 nanoparticle. (A) Characterization of oligochitosan nanoparticles. Atomic force microscope analysis of nanoparticles showing oligomeric structure complexed with DNA (red arrow). (B) Gene expression of chitosan-GFP in MDSC cells. Bar graph represents number of GFP positive cells per field. (C) Distribution of GFP in lung tissue. NG042 nanoparticles given intranasally to mice deliver genes to both the proximal and distal lung, as shown using the gene for GFP.

Figure 7:
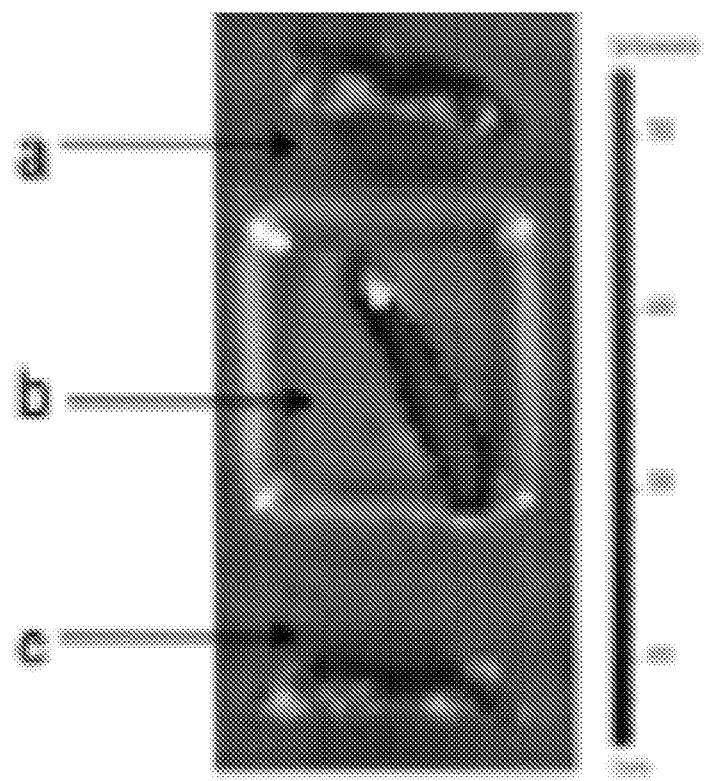

FIG. 7 illustrates that Chitosan-Ly6G-XL-680 targets and binds to MDSCs. Ten day-old EL-4 tumor-bearing mice were injected with chitosan only (A), chitosan-Ly6G-XL 680 (B), or chitosan-isotype antibody (C). After 24 hours, mice were imaged by Xenogen IVIS. The harvested spleen shows accumulation of chitosan-Ly6G-XL 680.

FIG. 8 illustrates that expansion of MDSC in aged humans is due to inflammation. Peripheral blood mononuclear cells (PBMC) from healthy volunteer donors (young and old-age) or asthmatics (n=22) were analyzed for the presence of MDSC (Lin$^-$HLADR$^-$CD33$^+$). One aliquot of cells was stimulated by LPS. (A) FACS analysis of MDSC. PBMCs were stained with cocktail of lineage-specific antibody (anti-CD3, CD14, CD19, and CD56), anti-HLA-DR antibody, and anti-CD33 antibody. Left, lineage-negative cells were gated; right, proportion of HLA-DR$^-$CD33$^+$ MDSC was determined; middle, staining with isotype control Ig. Lineage-negative cells were gated and percentage of HLA-DR$^-$CD33$^+$ MDSC was determined (B) Percentage of MDSC with and without LPS stimulation. (C) PBMC MDSCs from asthmatics and healthy donors were analyzed for the presence of Lin$^-$HLADR$^-$CD33$^+$ (D) Plasma IL-6 levels from young(less than 50 years) and old asthmatics (greater than 50 years) was analyzed by IL-6 ELISA. (E) Expression of mir-142/223 in MDSC. (F-H) Dendritic cells were gated as lineage-negative and HLA-DR-positive cells; right, within this population, CD11c$^+$CD123 cells represent myeloid dendritic cells (MDC) (F) and CD11c$^-$CD123$^+$ represent a population of plasmacytoid dendritic cells (PDC) (G). (H) Ratio of MDC/PDC.

Figure 9:
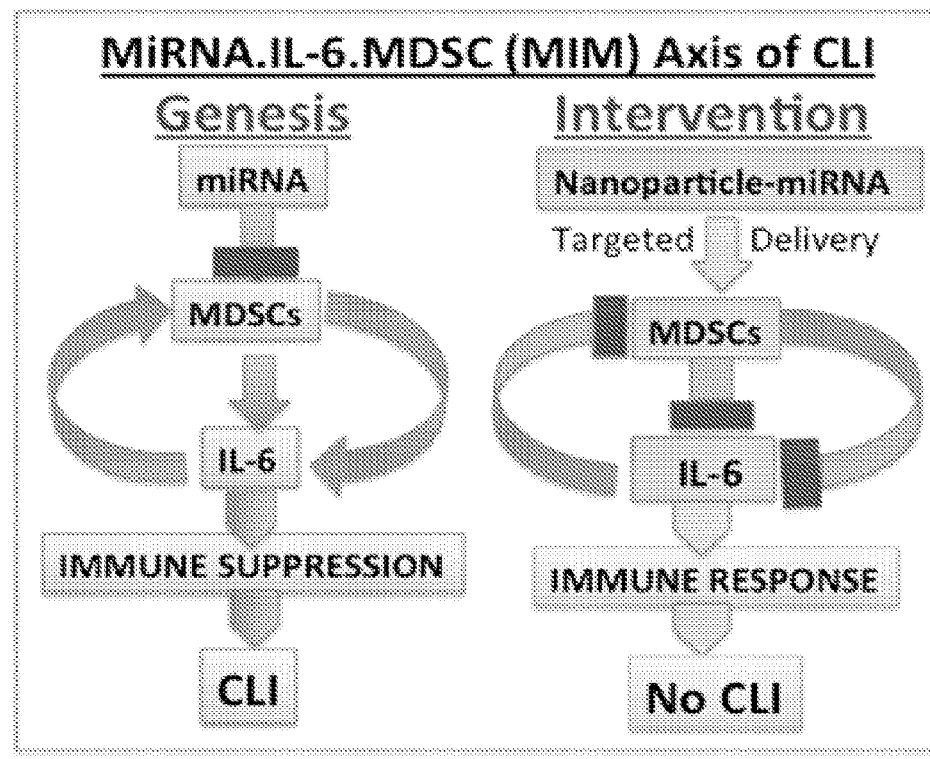

FIG. 9 shows a schematic proposed for the chronic lung inflammation (CLI) cascade and a method of interrupting the cascade.

DETAILED DESCRIPTION

Provided herein are methods and compositions for modulating the differentiation of a myeloid derived suppressor cell (MDSC). In particular, described herein are miR-142 polynucleotides and miR-223 polynucleotides that can be used to modulate differentiation of MDSCs. Increased differentiation of a MDSC population, or cells within an MDSC population, can be achieved by increasing the miR-142 and/or miR-223 ribonucleotides in a MDSC. Targeted delivery of miR-nanoparticles (nanoparticles comprising miRNA-142 and/or miRNA-223) to MDSCs in a subject can also redirect differentiation and alter immunity from 'suppressor' to "responder" mode. Such redirected differentiation methods can be used for the treatment of inflammatory diseases such as chronic lung inflammation and can also be harnessed to develop novel therapeutics for chronic inflammation.

The following definitions are used to delineate the meaning of words and terms used in this application for patent.

The singular form "a," "an" and "the" include plural references unless the context clearly dictates otherwise. For example, the term "a cell" includes a plurality of cells, including mixtures thereof.

When referring to a subject, the term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

The term "antibody" is used in the broadest sense, and specifically covers monoclonal antibodies (including full length monoclonal antibodies), polyclonal antibodies, and multispecific antibodies (e.g., bispecific antibodies). Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end.

The term "antibody fragment" refers to a portion of a full-length antibody, generally the target binding or variable region. Examples of antibody fragments include Fab, Fab', F(ab')$_2$ and Fv fragments. The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such molecule from having the ability to bind to the high affinity receptor, FcεRI. As used herein, "functional fragment" with respect to antibodies, refers to Fv, F(ab) and F(ab')$_2$ fragments. An "Fv" fragment is the minimum antibody fragment which contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Collectively, the six CDRs confer target binding specificity to the antibody. However, even a single variable domain (or half of an Fv comprising only three CDRs specific for a target) has the ability to recognize and bind target, although at a lower affinity than the entire binding site. "Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for target binding.

A "composition" is intended to mean a combination of active agent and another compound or composition, inert (for example, a detectable agent or label) or active, such as an adjuvant.

As used herein, the term "comprising" is intended to mean that the compositions and methods include the recited elements, but not excluding others. "Consisting essentially of," when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative".

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. DNA for a presequence or secretory leader may be operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

The terms "differentiation" and "differentiate" refer to the process by which precursor or progenitor cells (i.e., MDSCs) change into specific, and more mature, cell types, e.g., macrophages or dendritic cells. Differentiated macrophages and dendritic cells can be identified by their patterns of gene expression and cell surface protein expression. Typically, differentiated human macrophages express proteins such as F4/80 (EMR1), CD68, and MAC-1/MAC-2 on their surface. Typically, differentiated human dendritic cells express proteins such as CD11c and HLA-DR on their surface, and do not express, or have decreased expression of, CD123 and Lin on their surface. It should be understood that an increase in or induction of differentiation in a single cell includes the initiation, resumption, and/or completion of differentiation of the cell. An increase in differentiation in a population of cells includes an increase in the number of differentiated cells (i.e., macrophages and dendritic cells) in that population as compared to a control population of cells.

The term "dendritic cell" refers to cells in mice that express proteins such as CD11b, CD11c and IAb on their surface. The term "dendritic cell" also refers to cells in humans that express CD11c and HLA-DR on their surface, and do not express, or have decreased expression of, CD123 and Lin on their surface.

An "effective amount" is an amount sufficient to effect beneficial or desired results. An effective amount can be administered in one or more administrations, applications or dosages.

The Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art.

"Humanized" forms of non-human (e.g. murine) antibodies are chimeric immunoglobulins, immunoglobulin chains or fragments thereof (such as Fv, Fab, Fab', F(ab')$_2$ or other target-binding subsequences of antibodies) which contain minimal sequence derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin template chosen.

The term "isolated" means separated from constituents, cellular and otherwise, in which the polynucleotide, peptide, polypeptide, protein, antibody, or fragments thereof, are normally associated with in nature. In one aspect of this invention, an isolated polynucleotide is separated from the 3' and 5' contiguous nucleotides with which it is normally associated with in its native or natural environment, e.g., on the chromosome. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

The term "macrophage" refers to phagocytic cells in mice that express proteins such as CD11b and F4/80 on their surface. The term "macrophage" also refers to phagocytic cells in humans that express F4/80 (EMR1), CD68, and MAC-1/MAC-2 on their surface.

"Mammal" for purposes of treatment refers to any animal classified as a mammal, including human, domestic and farm animals, nonhuman primates, and zoo, sports, or pet animals, such as dogs, horses, cats, cows, etc.

The term "modulating" means changing and includes increasing or decreasing in amount or effect.

The term "myeloid derived suppressor cell" is used interchangeably with "MDSC" herein. These terms refer to cells in mice that display immune suppressor activity and express proteins such as CD11b and Gr-1 on their surface. These terms also refer to cells in humans that express proteins such as CD33 on their surface, do not express proteins such as Lin and HLA-DR on their surface, and display immune suppressor activity. Immune suppressor activity can be indicated by high arginase production, high iNOS production and/or ROS production. MDSCs can be divided into granulocytic and monocytic sub-types based upon their expression of CD14 protein (CD14 are monocytic and CD14$^-$ are granulocytic.) CD14 positive MDSCs may also express S100A9 protein on their surface and be identified accordingly.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single target site. Furthermore, in contrast to conventional (polyclonal) antibody preparations which typically include different antibodies directed against different determinants (epitopes), each monoclonal antibody is directed against a single determinant on the target. In addition to their specificity, monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SCI., 15th Ed. (Mack Publ. Co., Easton (1975)).

The term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount", "therapeutically effective amount" or "therapeutically effective dose" refer to the amount of composition containing a miRNA-142 polynucleotide and/or a miRNA-223 polynucleotide that will elicit the biological or medical response of a tissue, system, animal, or human that is being sought by the researcher, veterinarian, medical doctor, or other clinician. In some embodiments, the response is modulation of MDSC differentiation.

The terms "polynucleotide" and "oligonucleotide" are used interchangeably, and refer to a polymeric form of nucleotides of any length, either deoxyribonucleotides or ribonucleotides, or analogs thereof. As used herein, the term "polynucleotide" refers to either a miR-142 or a miR-223 ribonucleotide sequence or the deoxyribonucleotide sequence that encodes the miR-142 or a miR-223 ribonucleotide sequence. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, miRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The terms "prevent," "preventing," "prevention," and grammatical variations thereof as used herein, refer to a method of partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms.

A "subject," "individual" or "patient" is used interchangeably herein, which refers to a vertebrate, preferably a mammal, more preferably a human. Mammals include, but are not limited to, murines, simians, humans, farm animals, sport animals, and pets.

The terms "pharmaceutically effective amount", "therapeutically effective amount" or "therapeutically effective dose" refer to the amount of a compound such as a composition containing a miRNA-142 polynucleotide and/or a miRNA-223 polynucleotide that will elicit the biological or medical response of a tissue, system, animal, or human that is being sought by the researcher, veterinarian, medical doctor or other clinician.

The term "therapeutically effective amount" includes that amount of a compound such as a composition containing a miRNA-142 polynucleotide and/or a miRNA-223 polynucleotide that, when administered, is sufficient to prevent development of, or alleviate to some extent, one or more of the symptoms of the condition or disorder being treated. The therapeutically effective amount will vary depending on the compound such as a composition containing a miRNA-142 polynucleotide and/or a miRNA-223 polynucleotide, the disorder or conditions and its severity, the route of administration, time of administration, rate of excretion, drug combination, judgment of the treating physician, dosage form, and the age, weight, general health, sex and/or diet of the subject to be treated. In the context of the present method, a pharmaceutically or therapeutically effective amount or dose of a composition containing a miRNA-142 polynucleotide and/or a miRNA-223 polynucleotide includes an amount that is sufficient to increase differentiation of MDSCs in a given MDSC population in a subject as compared to a control subject.

"Transformation" of a cellular organism with DNA means introducing DNA into an organism so that the DNA is replicable, either as an extra chromosomal element or by chromosomal integration. "Transfection" of a cellular organism with DNA refers to the taking up of DNA, e.g., an expression vector, by the cell or organism whether or not any coding sequences are in fact expressed. The terms "transfected host cell" and "transformed" refer to a cell in which DNA was introduced. The cell is termed "host cell" and it may be either prokaryotic or eukaryotic. Typical prokaryotic host cells include various strains of E. coli. Typical eukaryotic host cells are mammalian, such as Chinese hamster ovary or cells of human origin. The introduced DNA sequence may be from the same species as the host cell of a different species from the host cell, or it may be a hybrid DNA sequence, containing some foreign and some homologous DNA.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. In some instances, the terms "treat," "treating," "treatment," and grammatical variations thereof, include reducing inflammation including, but not limited to, chronic lung inflammation, as compared with prior to treatment of the subject or as compared with the incidence of such symptom in a general or study population.

The term "variable" in the context of variable domain of antibodies, refers to the fact that certain portions of the variable domains differ extensively in sequence among antibodies and are used in the binding and specificity of each particular antibody for its particular target. However, the variability is not evenly distributed through the variable domains of antibodies. It is concentrated in three segments called complementarity determining regions (CDRs) also known as hypervariable regions both in the light chain and the heavy chain variable domains. The more highly conserved portions of variable domains are called the framework (FR). The variable domains of native heavy and light chains each comprise four FR regions, largely a adopting a .beta.-sheet configuration, connected by three CDRs, which form loops connecting, and in some cases forming part of, the .beta.-sheet structure. The CDRs in each chain are held together in close proximity by the FR regions and, with the CDRs from the other chain, contribute to the formation of the target binding site of antibodies. As used herein, numbering of immunoglobulin amino acid residues is done according to the immunoglobulin amino acid residue numbering system of Kabat et al., (Sequences of Proteins of Immunological Interest, National Institute of Health, Bethesda, Md. 1987), unless otherwise indicated.

Accordingly, provided herein are compositions and methods for modulating differentiation of a MDSC comprising modulating an amount of a miR-142 ribonucleotide and/or a miR-223 ribonucleotide in the cell. In some embodiments, the amount of miR-142 and/or miR-223 ribonucleotide in an MDSC is increased and differentiation of the MDSC is increased. The miR-142 and miR-223 ribonucleotides can be from any species, and in one embodiment, these ribonucleotides are human. The miR-142 ribonucleotide can be increased by transformation of the MDSC cell with a miR-142 deoxyribonucleotide. In some embodiments, the miR-142 deoxyribonucleotide comprises SEQ ID NO:1 gacagtgcagtcacccataaagtagaaagcactactaacagcactggagg gtgtagtgtttcctactttatggatgagtgtactgtg.

The miR-223 ribonucleotide can be increased by transformation of the MDSC cell with a miR-223 deoxyribonucleotide. In some embodiments, the miR-223 deoxyribonucleotide comprises SEQ ID NO:2:

cctggcctcctgcagtgccacgctccgtgtatttgacaagctgagttgga cactccatgtggtagagtgtcagtttgtcaaatacccaagtgcggcacat gcttaccag.

When a MDSC is transformed with a miR-142 and/or miR-223 deoxyribonucleotide, it is to be understood that the deoxyribonucleotide can be administered to the MDSC as a part of an expression plasmid, which expression plasmid contains one or more control sequences such as promoters, poly A sequences, etc., that are required for expression of the miR-142 and/or miR-223 deoxyribonucleotide in the MDSC. In some embodiments, the one or more control sequences allow for expression of a miR-142 and/or miR-223 deoxyribonucleotide in a human cell, preferably, a human MDSC.

A surprising finding described herein is that increasing the amount of miR-142 and/or miR-223 polynucleotide in a MDSC results in differentiation of the MDSC into a macrophage or dendritic cell. Accordingly, included herein are methods of differentiating a MDSC into a macrophage or dendritic cell by increasing the amount of miR-142 and/or miR-223 ribonucleotide in the MDSC. Also included herein are methods of differentiating a population of MDSCs into macrophages and/or dendritic cells by increasing the amount of miR-142 and/or miR-223 ribonucleotide in the MDSC that comprise the population. In some embodiments, a MDSC differentiates into an EMR1$^+$ CD68$^+$MAC-1/MAC-2$^+$ macrophage (or a macrophage that expresses EMR1, CD68 MAC-1/MAC-2 and on its surface). In other or further embodiments, a MDSC differentiates into a CD11c$^+$ HLADR$^+$CD123$^-$Lin$^-$ dendritic cell (or a dendritic cell that expresses CD11c and HLA-DR on their surface, and does not express, or has decreased expression of, CD 123 and Lin on its surface).

The miR-142 and miR-223 polynucleotides can be administered to a MDSC by any method known to those of skill in the art. In one embodiment, the miR-142 and/or miR-223 polynucleotide is administered to the MDSC using a nanoparticle. Accordingly, provided herein is a composition comprising a nanoparticle and a miR-142 polynucleotide and/or a miR-223 polynucleotide. In one embodiment, the miR-142 polynucleotide and/or a miR-223 polynucleotide is a deoxyribonucleotide. The miR-142 and/or miR-223 nanoparticle composition is administered to a MDSC cell to achieve an increase in the amount of miR-142 and/or miR-223 in the cell and to induce differentiation of the cell.

As used herein, the term "nanoparticle" refers to a material with overall dimensions in the nanoscale, i.e., under 100 nm. Nanoparticles include, but are not limited to, polymer-protein conjugates, polymeric micelles, liposomes, and chitosan-based nanoparticles. Polymer-protein conjugates most commonly use PEG. PEG is well known for its high water solubility and excellent biocompatibility, and its attachment to drugs results in increased solubility. PEG attachment is also known to reduce the renal clearance of drugs and enhance receptor-mediated uptake by cells. This approach can therefore be utilized to prolong the half-life of a drug and reduce dosing frequency. Polymeric micelles are typically created with amphiphilic polymers that form micelles in solution with a drug entrapped inside the micelles. Liposomes are vesicles formed by the entrapment of fluid by phospholipid molecules which have hydrophobic and hydrophilic components and can form bilayers.

In one embodiment, a chitosan/pmiR-142 nanoparticle is prepared by mixing chitosan (10 mg/ml) and plasmid expressing miR-142 (pmiR-142) (2 µg/ml) (ratio 1:5) solutions in phosphate buffer. Particle size and zeta potential of the chitosan/pmiR-142 nanoparticle are measured using a Microtrac Zetasizer. The morphological images are obtained by transmission electron microscopy (a Hitachi Model 7280 (Hitachi, Pleasanton, Calif.) Integrity of these nanoparticles is validated using agarose gel retardation assay along with non-encapsulated DNA as controls. The imaging arm Ly6G antibody conjugated to xenolight 680 is further mixed 1:1 with a colloidal suspension of chitosan-pmiR-142 nanoparticles.

The miR-142 and miR-223 polynucleotides may be combined with pharmaceutically acceptable carriers and administered to a MDSC as compositions in vitro or in vivo. In one embodiment, a composition comprising a miR-142 and/or miR-223 polynucleotide is administered to a MDSC in vitro in an amount effective to induce differentiation in the MDSC. The MDSC is then administered to a subject with a pharmaceutically acceptable carrier for reduction of an inflammatory response.

Inflammation promotes expansion of MDSC (Youn, J. I., Nagaraj, S., Collazo, M. & Gabrilovich, D. I. J Immunol 181, 5791-5802 (2008); Ray, P., Arora, M., Poe, S. L. & Ray, A. Immunologic research 50, 153-158 (2011); Cheng, P., et al. The Journal of Experimental Medicine 205, 2235-2249 (2008); Delano, M. J., et al. J Exp Med 204, 1463-1474 (2007); Gabrilovich, D. I. & Nagaraj, S. Nature reviews. Immunology 9, 162-174 (2009); Kusmartsev, S., Nagaraj, S. & Gabrilovich, D. I. Journal of immunology 175, 4583-4592 (2005); Nagaraj, S., et al. Nature medicine 13, 828-835 (2007)). Provided herein is data showing that in chronic inflammation/asthma, MDSC expand both locally in the lungs and systemically in the spleens. This data suggests that MDSCs play a pivotal role with regard to local and systemic immune defects in a chronic lung inflammation in aged populations. The data shows that both elderly humans and aged mice show increases in the number of MDSCs.

IL-6 is implicated in aged related disorders and asthma. Data provided herein demonstrates that MDSCs produce increased levels of IL-6 and are subject to autocrine regulation by IL-6. Corresponding to the increase in IL-6 a significant down regulation of miRs-142 and -223 expression was observed. Studies have associated miRs-142 and -223 with normal myeloid cell regulation and differentiation but not with regulation of MDSCs (Johnnidis, J. B., et al. Nature 451, 1125-1129 (2008)). Another study has shown an association between miRs-142 and regulation of IL-6 in dendritic cells (Sun, Y., et al. Blood 117, 6172-6183 (2011)). Also, allergen exposure and/or respiratory infections cause further increases in plasma levels of IL-6, which is known to be a target of miRs-142 (Sun, Y., et al. Blood 117, 6172-6183 (2011)).

Asthma is a complex chronic lung disease and the chronicity is progressive; therefore, its genesis may involve more than one pathway. It is hypothesized herein that the miR-142/IL-6/MDSC axis is a master regulator that perpetuates chronic lung inflammation, but other pathways such as those involving Tregs or Th17 cells may also be involved. There is also a likelihood of cross-talk among these pathways. There may exist a compensatory mechanism wherein other cell types like epithelial cells, type I or type II cells that are known to have a pleotropic effect on inflammation to produce IL-6 or other cytokines such as IL-17 or TGF-β to resolve chronic lung inflammation (CLI).

Provided herein is data showing that the expression of two miRNAs, miR-142 and miR-223, is significantly decreased in asthmatics compared to healthy controls. Also, in the mouse model of OVA-induced asthma and LPS and/or RSV-induced inflammation, the expression of these two miRNAs is reduced in the asthmatic/inflamed group compared to controls (FIG. 5, and FIG. 6). Both miR-142 (expressed at high level in spleen, lung and thymus) and miR-223 (expressed in BM) are present at low levels in hematopoietic cells and their expression increases steadily during granulocytic differentiation (Chen, C. Z., Li, L., Lodish, H. F. & Bartel, D. P. Science 303, 83-86 (2004); Fazi, F., et al. Cell 123, 819-831 (2005); Fukao, T., et al. Cell 129, 617-631 (2007)). Mice deficient in miR-223 have an increased number of both BM neutrophils and circulating neutrophils (neutrophilia) displaying hypermature morphology and aberrant expression of lineage specific markers (Johnnidis, J. B., et al. Nature 451, 1125-1129 (2008)). Furthermore, miR223 positively regulates miR142 (Sun, W., et al. Cell Res (2010)).

Further provided herein is data that overexpression of miRNA-142 in MDSCs is sufficient to differentiate them into antigen-presenting cells. In addition, miR-142-overexpressing Tg mice lack MDSC expansion—suggesting that therapeutic overexpression of miR-142 can induce MDSC differentiation and correct defective immunity. It is possible that miR-142 may not induce a complete correction or differentiation of MDSCs and that the expansion of MDSCs may also depend on miR-223. Because MDSCs in human studies and asthma show decreased expression of both miR-142 and miR-223, the latter being anti-neutrophilic and positive regulator of miR-142, it is hypothesized that therapeutic intervention to alter the differentiation of MDSCs can modulate chronic inflammation.

It is suggested herein that the accumulation of MDSCs leads to a sustained immunosuppressive environment and that continued/intermittent exposure to allergens and/or viral infection induces chronic inflammation accompanied by lung tissue damage in the elderly. An important new axis of CLI is set forth involving miRNA-regulated expression of IL-6 in MDSCs (MIM axis of CLI) initiating a self-perpetuating inflammatory cascade. This miRNA-inhibition of IL-6 from MDSCs is potentially reversible by manipulating miRNA expression and may be harnessed to develop novel therapeutics for CLI.

Accordingly, provided herein are methods wherein the miR-142 and miR-223 polynucleotides are combined with pharmaceutically acceptable carriers and administered to a MDSC as compositions in vitro or in vivo. In these embodiments, it is to be understood that the MDSC can be administered to the subject before, after or during its differentiation. MDSCs can be obtained from any source including the subject to which they are administered. In one embodiment, the MDSC is obtained from a blood sample. In another embodiment, the MDSC is obtained from a bone marrow sample.

It is to be further understood that one or more miR-142 and miR-223 polynucleotides may be administered to a MDSC in vitro either alone or in combination with other immunomodulatory agents that affect MDSCs, in an amount effective to induce differentiation of an MDSC that is designed to be re-injected to an animal or human. Immunomodulatory agents include, but are not limited to the following: aluminum hydroxide; aluminum phosphate; calcium phosphate; polymers; co-polymers such as polyoxyethylene-polyoxypropylene copolymers, including block co-polymers; polymer P1005; Freund's complete adjuvant (for animals); Freund's incomplete adjuvant; sorbitan monooleate; squalene; CRL-8300 adjuvant; QS 21; saponins; ISCOM; muramyl dipeptide; glucosaminylmuramyl dipeptide; trehalose; bacterial extracts, including mycobacterial extracts; bacterial whole cells, including mycobacterial whole cells; detoxified endotoxins; membrane lipids; DNA isolated from prokaryotic organisms, CpG synthetic oligonucleotides; non-CpG synthetic oligonucleotides; aptamers; plasmids immunostimulatory molecules; poly (I:C) molecules; cytokines; chemokines; chitosan and derivatives; hyaluronic acid and derivatives; cholera toxin; pertussis toxin; and, keyhole limpet hemocyanin, or combinations thereof. The miR-142 and miR-223 polynucleotides or miR-142 and miR-223 polynucleotides plus immunomodulatory agent can be added to MDSC in a single treatment or in multiple treatments, optionally at different concentrations, and over a period of time appropriate for the stimulation of differentiation in the MDSC. The miR-142 and miR-223 polynucleotides can be added before, at the same time, or after administration of the immunomodulatory agents.

In other embodiments, a composition comprising a miR-142 and/or miR-223 polynucleotide is administered to a MDSC in vivo in an amount effective to induce differentiation of the MDSC. The composition comprising a miR-142 and/or miR-223 polynucleotide can be targeted to an area inside the subject via any method known to those of skill in the art. In one embodiment, a nanoparticle comprising a miR-142 and/or miR-223 polynucleotide, chitosan, and an antibody such as Ly6G is administered to a subject for the targeting of the miR-142 and/or miR-223 polynucleotide to the spleen. Example 8 below demonstrates that a chitosan-based nanoparticle binds to MDSC in vivo and (FIG. 6) and further demonstrates that a chitosan-based nanoparticle can be targeted to the spleen using Ly6G antibody (FIG. 7).

Forms of in vivo administration include, but are not limited to, injections, solutions, creams, gels, implants, pumps, ointments, emulsions, suspensions, microspheres, particles, microparticles, nanoparticles, liposomes, pastes, patches, tablets, transdermal delivery devices, sprays, aerosols, or other means familiar to one of ordinary skill in the art. Pharmaceutical formulations of the present invention can be prepared by procedures known in the art using well-known and readily available ingredients. For example, the compounds can be formulated with common excipients, diluents, or carriers, and formed into tablets, capsules, suspensions, powders, and the like. Examples of excipients, diluents, and carriers that are suitable for such formulations include the following: fillers and extenders (e.g., starch, sugars, mannitol, and silicic derivatives); binding agents (e.g., carboxymethyl cellulose and other cellulose derivatives, alginates, gelatin, and polyvinyl-pyrrolidone); moisturizing agents (e.g., glycerol); disintegrating agents (e.g., calcium carbonate and sodium bicarbonate); agents for retarding dissolution (e.g., paraffin); resorption accelerators (e.g., quaternary ammonium compounds); surface active agents (e.g., cetyl alcohol, glycerol monostearate); adsorptive carriers (e.g., kaolin and bentonite); emulsifiers; preservatives; sweeteners; stabilizers; coloring agents; perfuming agents; flavoring agents; lubricants (e.g., talc, calcium and magnesium stearate); solid polyethyl glycols; and mixtures thereof.

The formulations can be so constituted that they release the active ingredient only or preferably in a particular location, possibly over a period of time (i.e., a sustained-release formulation). Such combinations provide yet a further mechanism for controlling release kinetics. The coatings, envelopes, and protective matrices may be made, for example, from polymeric substances or waxes.

Compositions comprising one or more miR-142 and/or miR-223 polynucleotide and a pharmaceutically acceptable carrier are prepared by uniformly and intimately bringing into association the miR-142 and/or miR-223 polynucleotide and the pharmaceutically acceptable carrier. Pharmaceutically acceptable carriers include liquid carriers, solid carriers or both. Liquid carriers are aqueous carriers, non-aqueous carriers or both, and include, but are not limited to, aqueous suspensions, oil emulsions, water-in-oil emulsions, water-in-oil-in-water emulsions, site-specific emulsions, long-residence emulsions, sticky-emulsions, microemulsions and nanoemulsions. Solid carriers are biological carriers, chemical carriers or both and include, but are not limited to, viral vector systems, particles, microparticles, nanoparticles, microspheres, nanospheres, minipumps, bacterial cell wall extracts and biodegradable or non-biodegradable natural or synthetic polymers that allow for sustained release of the oligonucleotide compositions. Emulsions, minipumps and polymers can be implanted in the vicinity of where delivery is required (Brem et al., J. Neurosurg. 74: 441, 1991). Methods used to complex miR-142 and/or miR-223 polynucleotide to a solid carrier include, but are not limited to, direct adsorption to the surface of the solid carrier, covalent coupling to the surface of the solid carrier, either directly or via a linking moiety, and covalent coupling to the polymer used to make the solid carrier. Optionally, a sequence(s) can be stabilized by the addition of non-ionic or ionic polymers such as polyoxyethylenesorbitan monooleates (TWEENs) or hyaluronic acid.

Preferred aqueous carriers include, but are not limited to, water, saline and pharmaceutically acceptable buffers. Preferred non-aqueous carriers include, but are not limited to, a mineral oil or a neutral oil including, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, soybean oil, canola oil, palm oil, olive oil and myglyol, wherein the fatty acids can be saturated or unsaturated. Optionally, excipients may be included regardless of the pharmaceutically acceptable carrier used to present the miR-142 and/or miR-223 polynucleotide compositions to cells. These excipients include, but are not limited to, anti-oxidants, buffers, and bacteriostats, and may include suspending agents and thickening agents.

One or more miR-142 and/or miR-223 polynucleotide may be administered to a human or an animal alone, or in combination with other immunomodulatory modalities including, but not limited to, the following: aluminum hydroxide; aluminum phosphate; calcium phosphate; polymers; co-polymers such as polyoxyethylene-polyoxypropylene copolymers, including block co-polymers; polymer P1005; Freund's complete adjuvant (for animals); Freund's incomplete adjuvant; sorbitan monooleate; squalene; CRL-8300 adjuvant; QS 21; saponins; ISCOM; muramyl dipeptide; glucosaminylmuramyl dipeptide; trehalose;

bacterial extracts, including mycobacterial extracts; bacterial whole cells, including mycobacterial whole cells; detoxified endotoxins; membrane lipids; DNA isolated from prokaryotic organisms, CpG synthetic oligonucleotides; non-CpG synthetic oligonucleotides; apatamers; plasmids encoding immunostimulatory molecules; poly (I:C) molecules; cytokines; chemokines; chitosan and derivatives; hyaluronic acid and derivatives; cholera toxin; pertussis toxin and keyhole limpet hemocyanin or combinations thereof.

Methods of administering the miR-142 and/or miR-223 polynucleotide of the present invention, MDSC containing the miR-142 and/or miR-223 polynucleotide, or compositions comprising miR-142 and/or miR-223 polynucleotide and other materials such as carriers of the present invention that are particularly suitable for various forms include, but are not limited to the following types of administration, intravenous, intraarterial, transdermal, intradermal, subdermal, subcutaneous, intramuscular, intratissular (e.g., tissue or gland), intrauterine, vaginal, into a body cavity, oral (e.g., buccal or sublingual), anal, rectal, as a suppository, topical, parenteral, nasal, aerosol, inhalation, intrathecal, intraperitoneal, into the lumen or parenchyma of an organ, into bone marrow and into any mucosal surface of the gastrointestinal, reproductive, urinary and genitourinary system. Techniques useful in the various forms of administrations mentioned above include but are not limited to, leukapheresis, topical application, ingestion, surgical administration, injections, sprays, transdermal delivery devices, osmotic pumps, electrodepositing directly on a desired site, or other means familiar to one of ordinary skill in the art.

The compositions of the present invention can be applied in the form of creams, gels, solutions, suspensions, liposomes, particles, or other means known to one of skill in the art of formulation and delivery of the compositions. Ultrafine particle sizes can be used for inhalation delivery of therapeutics. Some examples of appropriate formulations for subcutaneous administration include, but are not limited to, implants, depot, needles, capsules, and osmotic pumps. Some examples of appropriate formulations for vaginal administration include but are not limited to creams and rings. Some examples of appropriate formulations for oral administration include but are not limited to: pills, liquids, syrups, and suspensions. Some examples of appropriate formulations for transdermal administration include but are not limited to gels, creams, pastes, patches, sprays, and gels. Some examples of appropriate delivery mechanisms for subcutaneous administration include, but are not limited to, implants, depots, needles, capsules, and osmotic pumps. Formulations suitable for parenteral administration include, but are not limited to, aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. Extemporaneous injection solutions and suspensions may be prepared from sterile powders, granules and tablets commonly used by one of ordinary skill in the art.

Embodiments in which the compositions described herein are combined with, for example, one or more pharmaceutically acceptable carriers or excipients may conveniently be presented in unit dosage form and may be prepared by conventional pharmaceutical techniques. Such techniques include the step of bringing into association the compositions containing the active ingredient and the pharmaceutical carrier(s) or excipient(s). In general, the formulations are prepared by uniformly and intimately bringing into association the active ingredient with liquid carriers. Preferred unit dosage formulations are those containing a dose or unit, or an appropriate fraction thereof, of the administered ingredient. It should be understood that in addition to the ingredients particularly mentioned above, formulations comprising the compositions of the present invention may include other agents commonly used by one of ordinary skill in the art.

The volume of administration will vary depending on the route of administration. Such volumes are known to one of ordinary skill in the art of administering compositions to animals or humans. Depending on the route of administration, the volume per dose is preferably about 0.001 to 100 ml per dose, more preferably about 0.01 to 50 ml per dose and most preferably about 0.1 to 30 ml per dose. For example, intramuscular injections may range in volume from about 0.1 ml to 1.0 ml. The oligonucleotide compositions administered alone, or together with other therapeutic agent(s), can be administered in a single dose treatment, in multiple dose treatments, or continuously infused on a schedule and over a period of time appropriate to the disease being treated, the condition of the recipient and the route of administration. Moreover, the other therapeutic agent can be administered before, at the same time as, or after administration of the miR-142 and/or miR-223 polynucleotide compositions.

Preferably, the amount of miR-142 and/or miR-223 polynucleotide administered per dose is from about 0.0001 to 100 mg/kg body weight, more preferably from about 0.001 to 10 mg/kg body weight and most preferably from about 0.01 to 5 mg/kg body weight. The particular miR-142 and/or miR-223 polynucleotide, the amount per dose, the dose schedule and the route of administration should be decided by the practitioner using methods known to those skilled in the art and will depend on the type of disease, the severity of the disease, the location of the disease and other clinical factors such as the size, weight and physical condition of the recipient. In addition, in vitro assays may optionally be employed to help identify optimal ranges for sequence and for sequence plus therapeutic agent administration.

It should be understood that the foregoing relates to preferred embodiments of the present disclosure and that numerous changes may be made therein without departing from the scope of the disclosure. The disclosure is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present disclosure and/or the scope of the appended claims. All patents, patent applications, and publications referenced herein are incorporated by reference in their entirety for all purposes.

EXAMPLES

Example 1

OVA-Allergic Mice Show MDSC Expansion and miRNA Down Regulation

To test whether MDSCs expand in antigen-mediated airway inflammation, C57BL/6 mice were sensitized and challenged with OVA and controls were sensitized with OVA and challenged with PBS.[12,35] Unless otherwise stated, mice were purchased from the Jackson Laboratory (Bar Harbor, Me.), restriction enzymes from New England Biolabs Inc. (Beverly, Mass., USA), chemicals form Sigma-Aldrich (St. Louis, Mo.) and cell lines from American Type Culture Collection (ATCC, Rockville, Md.), Oligonucleotides (Oligo) and probes were synthesized by International DNA Technologies (IDT, Coralville, Iowa). A clinically relevant mouse model of asthma was established using a model antigen, ovalbumin (OVA) through systematic sensitization and intranasal challenge. Groups of 6 week-old female C57/BL6 (n=6) were primed by OVA/alum or alum by i.p. injection of 50 μg of OVA or adjuvant on days 1 and 14 and challenged intranasally (i.n.) with OVA or PBS on day 17, 19 and 21. Some mice were challenged with RSV in day 22. The successful establishment of the asthma model was confirmed by pulmonary inflammation and AHR (airway hyper reactivity) measurements. Lung sections were stained with hematoxylin and eosin (H & E). All animal studies were reviewed and approved by the Institutional Animal Care and Use Committee of the University of South Florida and are in accordance with the guidelines of the Department of Health and Human Services.

Figure 1A:
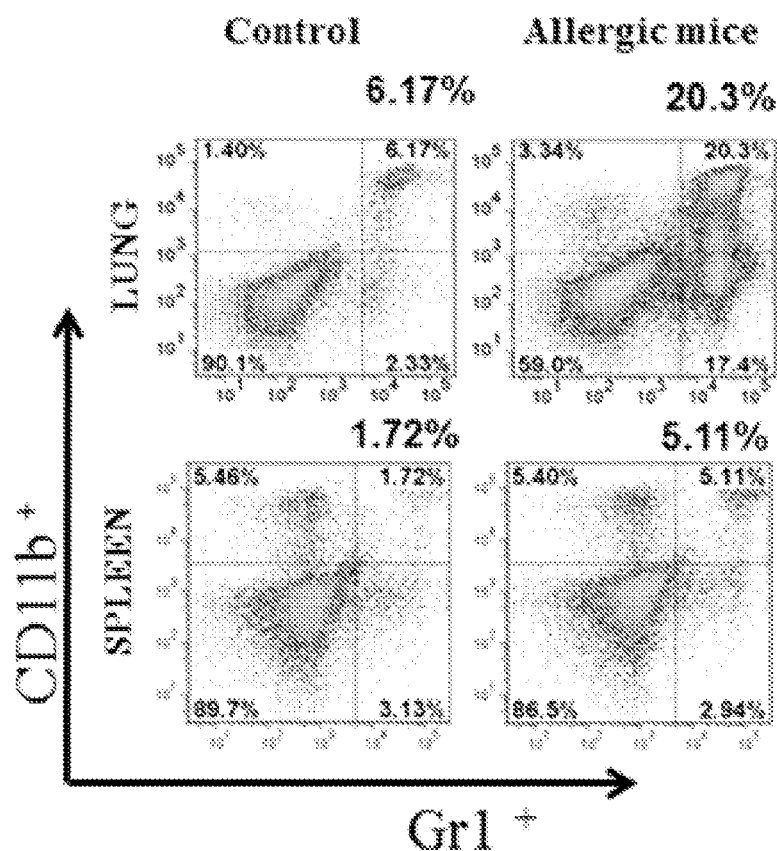
FIG. 1 illustrates that OVA-allergic mice show MDSC expansion and miRNA down regulation. C57BL/6 mice were sensitized at day 0 and challenged with OVA at day 18, 21, and 23. Spleen, lung tissue and BAL were isolated at day 25. (A) Dot blot represents expansion of MDSCs in lung (upper panel) and spleen (lower panel). (B) Lung histology sections from OVA-sensitized and control mice. (C) Bar graph represents miRs-223 and 142 expressions. (D) T cells from OT-I Tg mice were stained with CFSE and cultured with MDSC from naïve and OVA-allergic mice. Bars represent normalized percent of dividing cells in different generations.
Figure 1B:
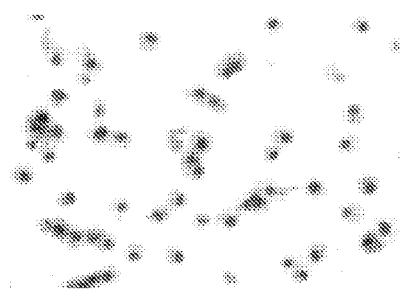
Figure 1B:
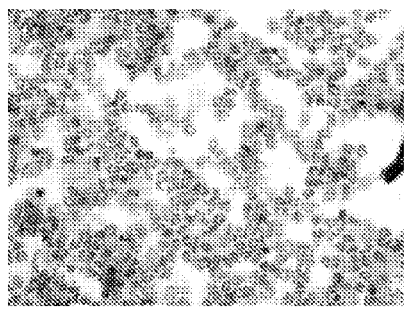
Figure 1B:
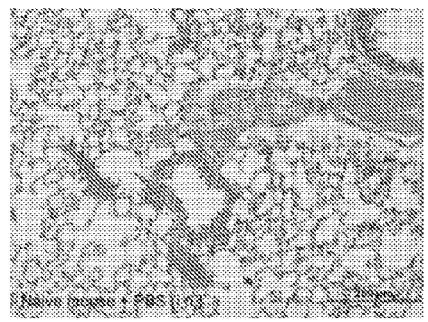
Figure 1B:
Figure 1C:
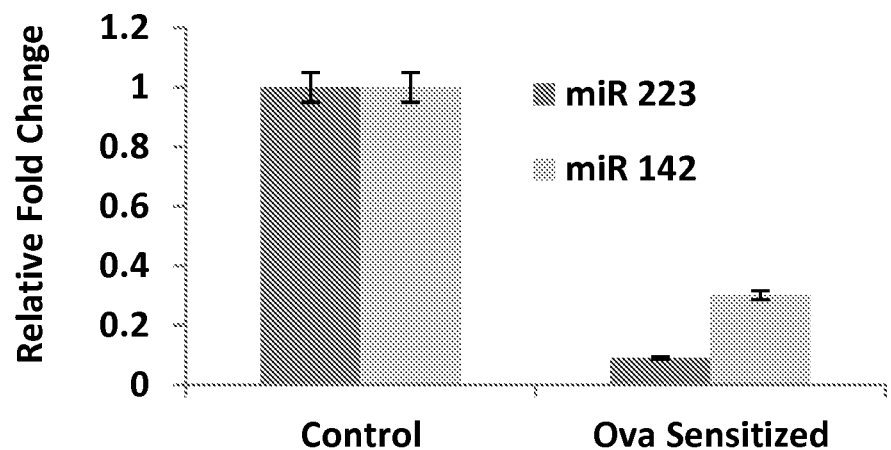

As a result of the sensitization and OVA challenge, MDSCs were expanded in lungs [control 6.17% versus allergic 20.3%] and spleens [control 1.72% versus allergic 5.11%] (FIG. 1A). Further, it was determined that systemic expansion of MDSCs in OVA-allergic mice was associated with a significant increase in inflammation in the BAL and lung (FIG. 1B) and a reduction in the expression of miRs-223 and -142 in MDSCs from spleens (FIG. 1C).

To test the functional consequence of MDSC expansion on T cells, isolated MDSCs were tested for the ability to suppress antigen specific activation of T cells. MDSC were isolated from spleens and lungs of asthmatic aged mice using biotinylated anti-Gr-1 antibody and MiniMACS columns (Miltenyi Biotec GmbH). This resulted in more than 95% purity of Gr-1+CD11b+ cells. T lymphocytes were isolated from spleens using T-cell enrichment columns (R&D Systems).

Figure 1D:
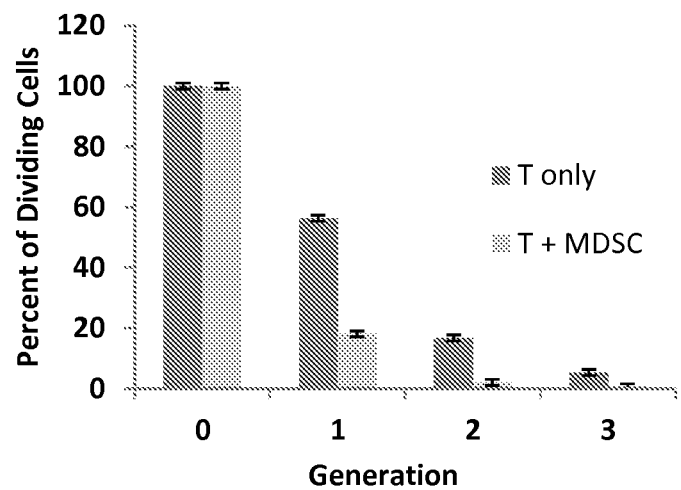

Once isolated, T cells from OT-I Tg mice were stained with CFSE and cultured with MDSC from naïve and OVA-allergic mice. The results are shown in FIG. 1D where bars represent normalized percent of dividing cells in different generations. The figure shows antigen specific inhibition of T cell proliferation.

Example 2

Expansion of MDSC in Aged Mice

Figure 2A:
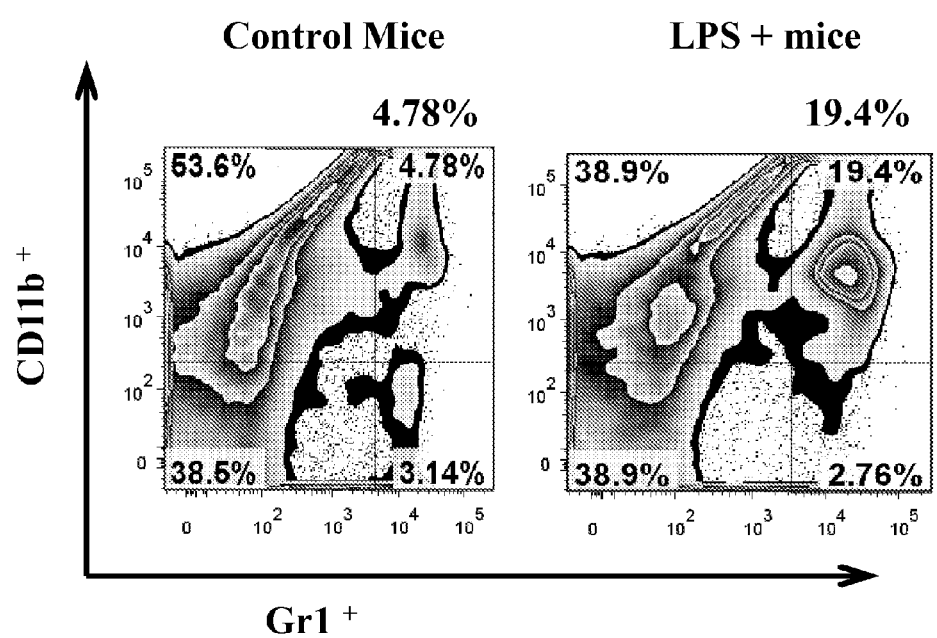
FIG. 2 illustrates expansion of MDSC in the aged. (A) Mice were injected with 100 μg of LPS twice on day 0 and day 3. Splenocytes were stained with DAPI, CD11b, and Gr1 antibodies. The percent of $CD11b^+Gr1^-$ cells in spleen from naïve or LPS-injected mice was determined by FACS analysis. (B) MDSCs were isolated from C57BL6 mice injected i.p. with 100 μg LPS twice on day 0 and day 3. miRNAs were then extracted and analyzed for miR-142 and -223 by real-time PCR and compared to three assay controls. Bars denote miR-142/-223 expression as relative fold increase. (C) MDSCs were isolated from young (6-8 week) and aged (less than 18 month old) mice. FACS analysis showed a substantial increase in the $CD11b^+ Gr1^+$ population was seen in aged mice compared to young. (D) MDSCs were isolated from young (6-8 week) and aged (less than 18 month old) mice. The miRNAs were then extracted and analyzed for miR-142 and -223 by real-time PCR and compared to three assay controls. Bars denote miR-142/-223 expression as relative fold increase. (E) Aged mice were injected with 25 μg LPS i.p. on day 0 and 3. On day 5, mice were infected with RSV $10^6$ pfu i.n. Day 10 spleens were harvested and cells were stained with CD11b, Gr1 and IL-6. The bar represents percent of miR-142/-223 expression and the green triangle shows the percentage of IL-6 producing MDSCs.

To investigate whether LPS-induced inflammation expands MDSC in aged mice, C57BL/6 mice were injected with LPS in on day 0 and day 3 and splenocytes were analyzed for frequency of the different myeloid cell subsets. Blood was drawn from young (less than 2 months old) (n=10) and old C57BL/6 mice (greater than 24 months old) (n=10) and analyzed for CD11b$^+$Gr1$^+$ (FIG. 2A). A substantial increase in the CD11b$^+$Gr1$^+$ population was seen (FIG. 2C) in aged mice compared to young. Accordingly, in aged mice there was a significant expansion (p<0.05) of MDSCs.

Example 3

Inflammation and Viral Infection Increases MDSC and IL-6 Production

In order to study systemic inflammatory changes related to age and airway inflammation, acute inflammation was induced in mice by LPS injection and followed by RSV infection. More particularly, aged C57BL/6 mice (less than 18 months old) were injected intraperitoneally with a low dose of LPS and then inoculated intranasally with $10^6$ PFU RSV (Chavez-Bueno, S., et al. Virol J 2, 46 (2005)). Five days later, blood was taken and spleens and lungs removed to test for inflammation. Surprisingly, mice injected with LPS and infected with RSV not only had increased viral titers but also showed expansion of IL-6-producing MDSCs compared to control mice or mice injected only with LPS or RSV (FIG. 2E). In the aged mice, a marked elevation of IL-6 production was observed for up to at least 5 days post RSV infection in contrast to young mice, which only lasted for 24 hours (data not shown). Corresponding to the increase in IL-6, a significant down regulation of miRs-142 and -223 expression in lung (data not shown) and spleen MDSCs (FIG. 2E) was also observed.

Example 4

Role of miR-142 in Aging

Utilizing an innovative high-throughput miRNA profiling system, a group of miRNAs was identified that appear to play critical roles in lung inflammation in mice (Wang, J.-w. P. L., Kunyu B S; Hellermann, Gary; Lockey, Richard F.; Mohapatra, Subhra; Mohapatra, Shyam. World Allergy Organization Journal 4, 94-103 (2011)). To confirm the role of two of these miRNAs, C57BL/6 mice were injected with LPS twice on day 0 and day 3, then CD11b$^+$Gr1 cells (MDSCs) were obtained from inflamed spleens and miRNA was isolated. MDSCs were evaluated for the expression of miRs-142 and -223 by qRT-PCR. For the qRT-PCR procedure, RNA was extracted with an RNase Mini kit and cDNA was synthesized using SuperScript III Reverse Transcriptase kit (QIAGEN, Valencia, Calif.). As previously described, PCR was performed with 2.5 μl cDNA, 12.5 μl SYBR Master Mixture (Applied Biosystems, Foster City, Calif.), and targeted gene-specific primers (Nefedova, Y., Cheng, P., Alsina, M., Dalton, W. S. & Gabrilovich, D. I. Blood 103, 3503-3510 (2004)). Amplification of endogenous β-actin, cyclophillin and GAPDH was used as an internal control.

Figure 2B:
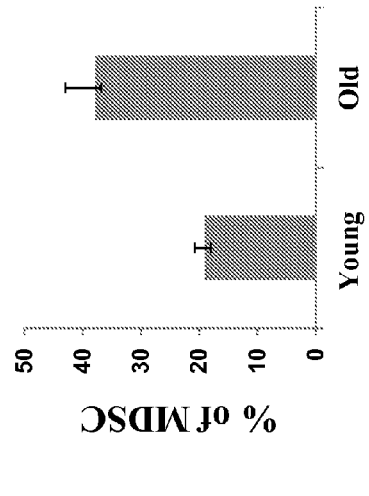
Figure 2C:
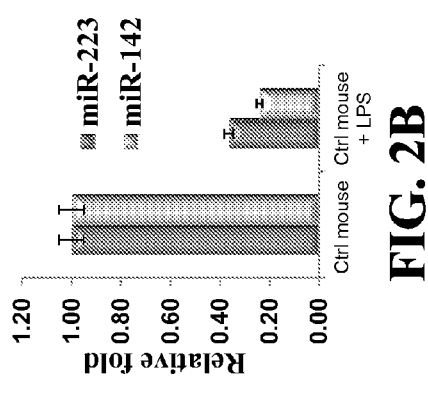
Figure 2D:
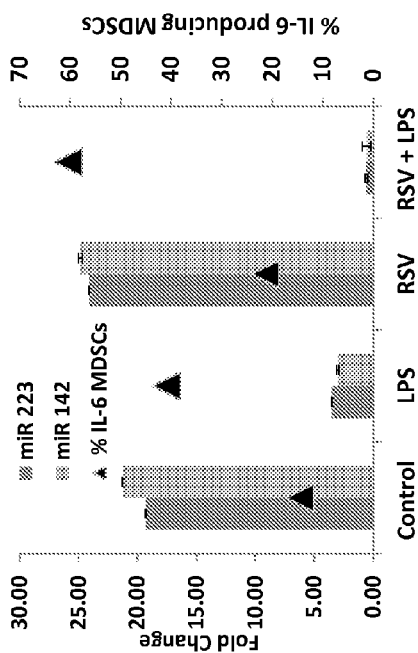
Figure 2E:
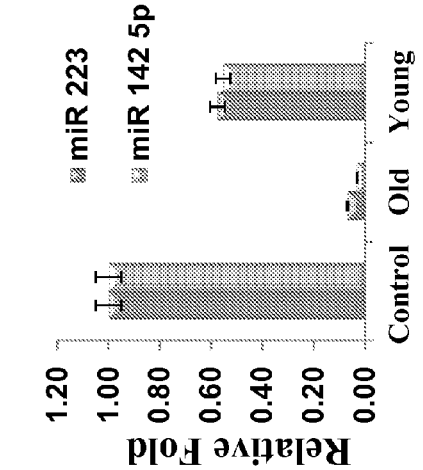

Data confirmed that MDSCs from inflamed mice down regulated expression of miRs-142 and -223 compared to CD11b$^+$Gr1$^+$ cells from naïve mice (FIG. 2B). Similar results were obtained when mice were challenged with OVA or RSV (FIG. 1D and data not shown). In another experiment, spleen cells were harvested from young and old mice and MDSCs were examined for miRs-142 and -223. The results show that MDSCs from old mice had significantly lower expression of miRNA-142 and -223 compared to young mice (FIG. 2D). These findings suggest that miRs-142 and -223 play a role in inflammation-mediated expansion of MDSCs.

Example 5

Development of miR-142 Tg Mice

A transgenic mouse was developed that overexpresses miR-142. Briefly, the pre-miR-142 sequence flanked with the adjacent sequences required for the processing of pre-miR-142 was cloned into pCAGEN vector (plasmid 11160, Addgene, Cambridge, Mass.). The positive clones were confirmed by sequencing and transfected into HK293 cells using Lipofectamine 2000. The miRNA expression levels in HK293 cells were then detected by real-time PCR. For generation of transgenic mice, the miR-142 transgene construct was linearized and transgenic mice were generated by pronuclear injection at Moffitt transgenic core facility (Tampa, Fla.). Founders were identified by genotyping and the overexpression of miR-142 in various tissues was confirmed by reverse transcription and quantitative real-time polymerase chain reaction (RT-qPCR).

Figure 3A:
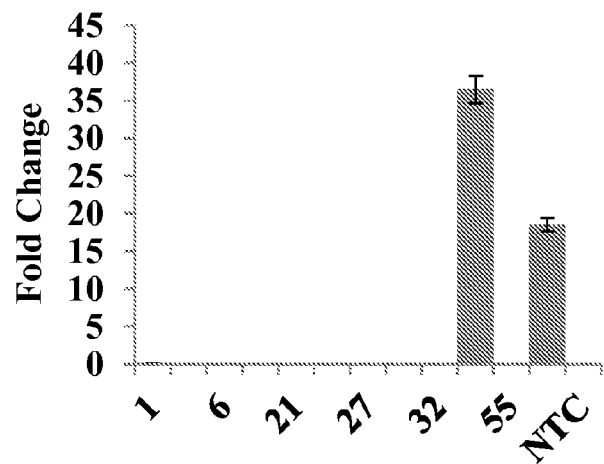
FIG. 3 illustrates RT PCR genotyping of 63 miR Tg mice using CAGEN-miR-142 primers. Initially, 63 samples were screened by individual primer pairs (CAGEN-miR-142), and then positive samples and adjacent samples were re-genotyped using specific primers. (A) Two positives were identified NTC, no template control. (B) miR-142 expression levels in the lungs of Tg and WT mice from the same litter. Bars represent fold change of miRNA expression (Tg/WT). (C) miR-142 expression in MDSCs isolated from spleens of WT and Tg mice. (D) Typical example of CD11b and Gr1 flow analysis from a peripheral blood sample.
Figure 3B:
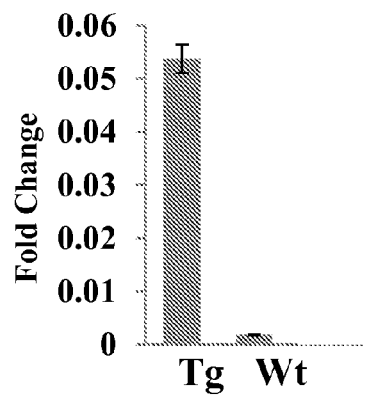
Figure 3C:
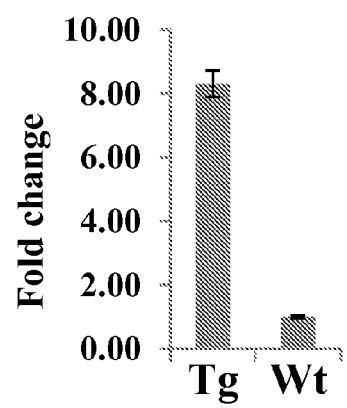
Figure 3D:
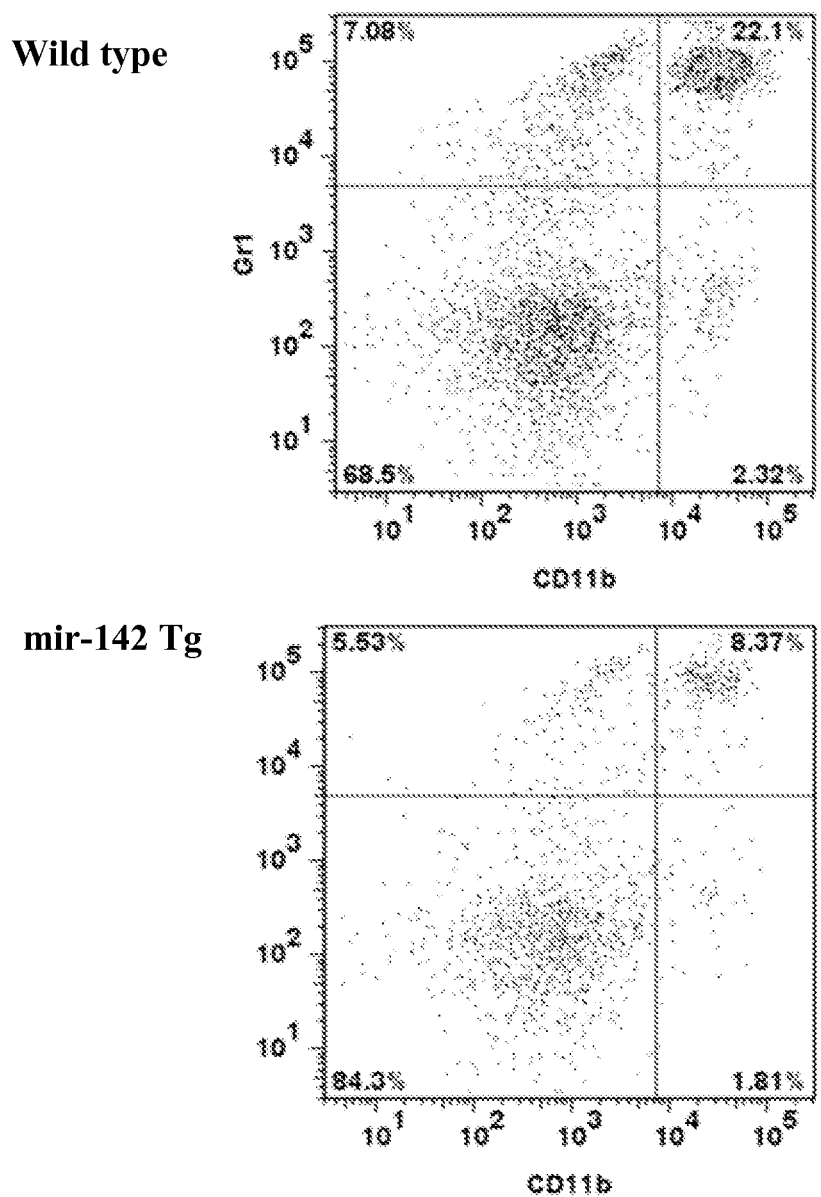

Real-time PCR genotyping of 63 miR transgenic mice using CAGEN-miR-142 primers resulted in two transgenic strains of mice (FIG. 3A) It was determined that miR-142 was overexpressed in the representative lung tissue (FIG. 3B) and MDSC (FIG. 3C). These Tg mice also had a significantly lower percent of MDSC in blood than the wildtype (FIG. 3D), but did not have any other developmental anomalies.

Example 6

MiR-142-tg Mice Fail to Expand MDSCs

Figure 4A:
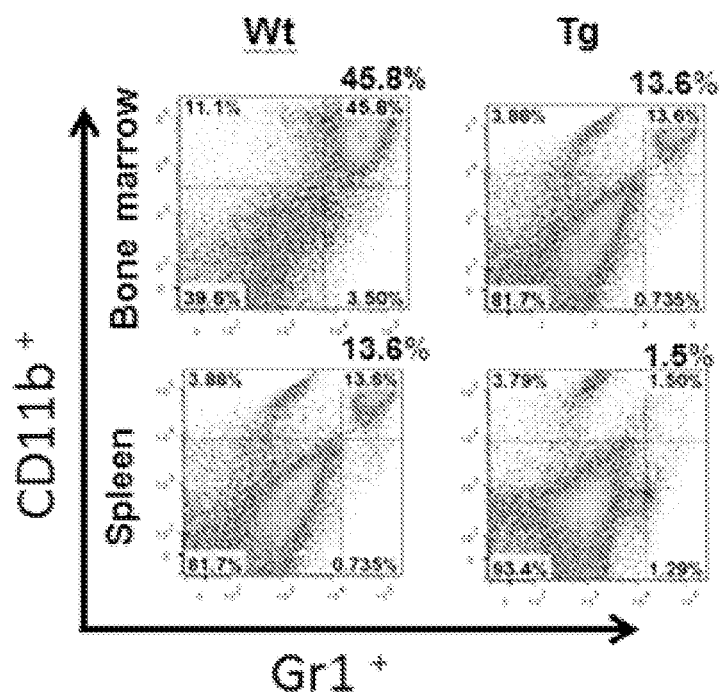
FIG. 4 illustrates that miR-142 inhibits MDSC expansion and IL-6 production. (A-B) WT or miR-142 Tg mice were injected 100 μg i.p. LPS on day 0 and day 3. On day 6, BM cells and splenocytes were analyzed for the percent of MDSC. (A) Numbers above denote the percentage of MDSC in the samples. (B) IL-6 expression in MDSC. (C)

To determine if overexpression of miR-142 blocks expansion of MDSCs, inflammation was induced by injecting LPS i.p. into wild-type (WT) and Tg mice. Very few MDSCs were identified in the bone marrow (BM) cells [13.4%] and splenocytes [1.5%] of Tg mice compared to WT [BM 45.8% and Spleen 13.6%] mice. (FIG. 4A) These results demonstrate that overexpression of miR-142 ablates in vivo accumulation of MDSC.

Figure 4C:
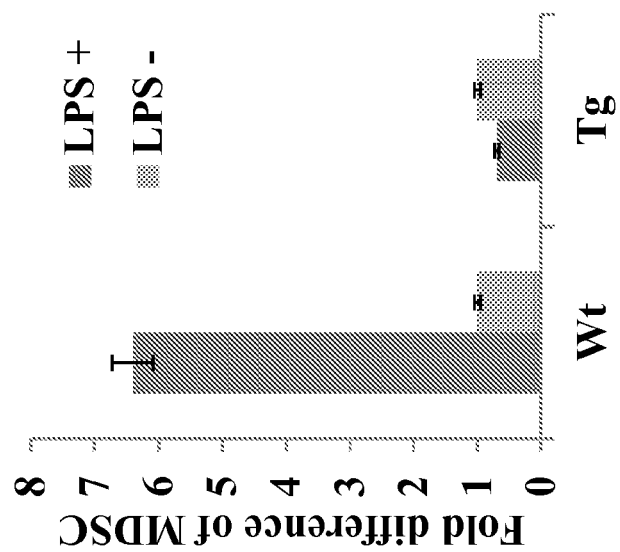
Figure 4B:
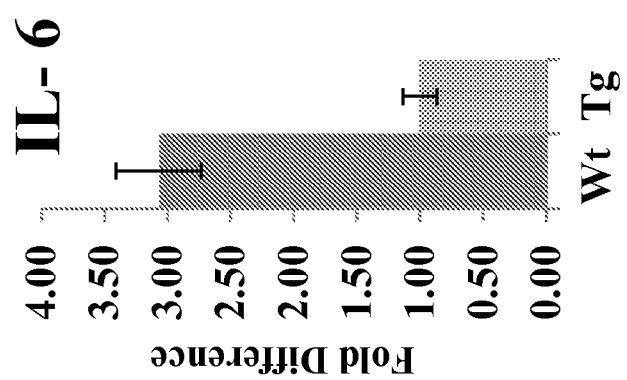

Correspondingly, MDSCs from Tg mice expressed lower levels of IL-6 (FIG. 4B). In another experiment, BM cells from WT and Tg mice were cultured with LPS, which induces in vitro expansion of MDSC (i.e. expansion of undifferentiated myeloid cells); however, BM cells of Tg mice failed to expand MDSC (FIG. 4C). These results show that miR-142 may directly or indirectly regulate expansion of MDSCs during inflammation via IL-6.

Example 7

BM Differentiation to MDSC is Associated with Decreased Expression of miR-142

To investigate the role of miR-142 in differentiation of MDSCs, BM cells were isolated from C57BL/6 mice and cultured with GM-CSF and tumor explant supernatant (TES described in Herber, D. L., et al. Nat Med 16, 880-886 (2010)) to induce inflammation. The BM cells were also cultured with GM-CSF and IL-4 to generate DCs. MDSCs and DCs were sorted and cells were isolated on day 7. Total miRNA was extracted and analyzed for the expression of miR-142 by RT-PCR. MiR-142 expression was down regulated only in the undifferentiated MDSCs and not in the differentiated DCs (FIG. 5A). These findings suggest a possible role of miR-142 in differentiation of MDSCs. Overexpression of miR-142 may negatively regulate expansion and differentiation of the MDSC subsets into DCs and macrophages.

Example 8

Nanoparticle-pmiR-142 Complexes Induce MDSC Differentiation

To investigate the potential to direct differentiation of MDSCs by overexpression of miR142, BM-derived MDSCs were isolated and incubated with nanoparticle-pmiR142 complexes. miR-142 chitosan nanospheres were generated as described previously. Briefly, 10 µg of miR-142 plasmid (pmiR-142, Origene, SC400778, MI0000167) was complexed with a nanochitosan polymer (50 µg). The pmiR-142 plasmid operably links a miR-142 deoxyribonucleotide with a CMV promoter and a poly A sequence. Resultant nanoparticles were examined immediately by light microscopy and stored at room temperature until use. Chitosan was conjugated with the total DNA concentration in the solution equally contributed by the component plasmids (10 µg of each plasmid/mouse).

As shown in FIG. 5B, pmiR-142 was successfully overexpressed in MDSCs. Further, MDSCs transfected with pmiR-142 differentiated to CD11b$^+$T4/80$^+$ macrophages or DCs (FIG. 5D) but not CD11b$^-$Gr1$^+$ MDSCs (FIG. 5C). These findings indicate that introduction of miR-142 can differentiate MDSCs into mature DCs and macrophages. Such differentiation may abrogate the inhibitory effects of inflammatory factors.

FIG. 6 illustrates the development and characterization of a chitosan-GFP (green fluorescent protein) nanoparticle that demonstrated the ability of the chitosan nanoparticles to deliver the miR-142 and miR-223 to cells in vivo. FIG. 6(A) shows an atomic force microscope analysis of nanoparticles demonstrating oligomeric structure complexed with DNA (red arrow). FIG. 6(B) shows gene expression of GFP in MDSC cells as delivered by chitosan-GFP nanoparticles, where the bar graph represents number of GFP positive cells per field. FIG. 6(C) shows the distribution of GFP in lung tissue after the chitosan-GFP nanoparticles were given intranasally to mice. GFP was expressed in both the proximal and distal lung.

FIG. 7 further illustrates that Chitosan-Ly6G-XL-680 targets and binds to MDSCs. Ten day-old EL-4 tumor-bearing mice were injected with chitosan only (A), chitosan-Ly6G-XL 680 (B), or chitosan-isotype antibody (C). Ly6G antibody binds to splenic cells, and XL-680 is a near-infrared flourochrome. After 24 hours, mice were imaged by Xenogen IVIS. The harvested spleen shows accumulation of chitosan-Ly6G-XL 680.

Example 9

Chronic Asthmatics have Increased Expansion of MDSC

The role of MDSC in a cohort of young, old, asthmatics and healthy individuals was examined. Peripheral blood mononuclear cells (PBMCs) were isolated from voluntary donors and cryopreserved in freezing media containing 50% RPMI-1640-1640, 40% FBS, and 10% DMSO and stored in liquid nitrogen. All samples from each patient were analyzed simultaneously. Briefly, PBMCs were thawed and labeled with lineage-specific phycoerythrin-conjugated antibodies against CD3, CD19, CD56, and CD14, anti-HLA-DR and allophycocyanin-conjugated anti-CD33 (all from BD Pharmingen, San Jose, Calif.). The phenotype of the cells was evaluated by multicolor flow cytometry using a FACSARIA cytometer (BD Biosciences, Mountain View, Calif.) and DAPI negative viable cells were analyzed using Flowjo ver 9.2.

Figure 8A:
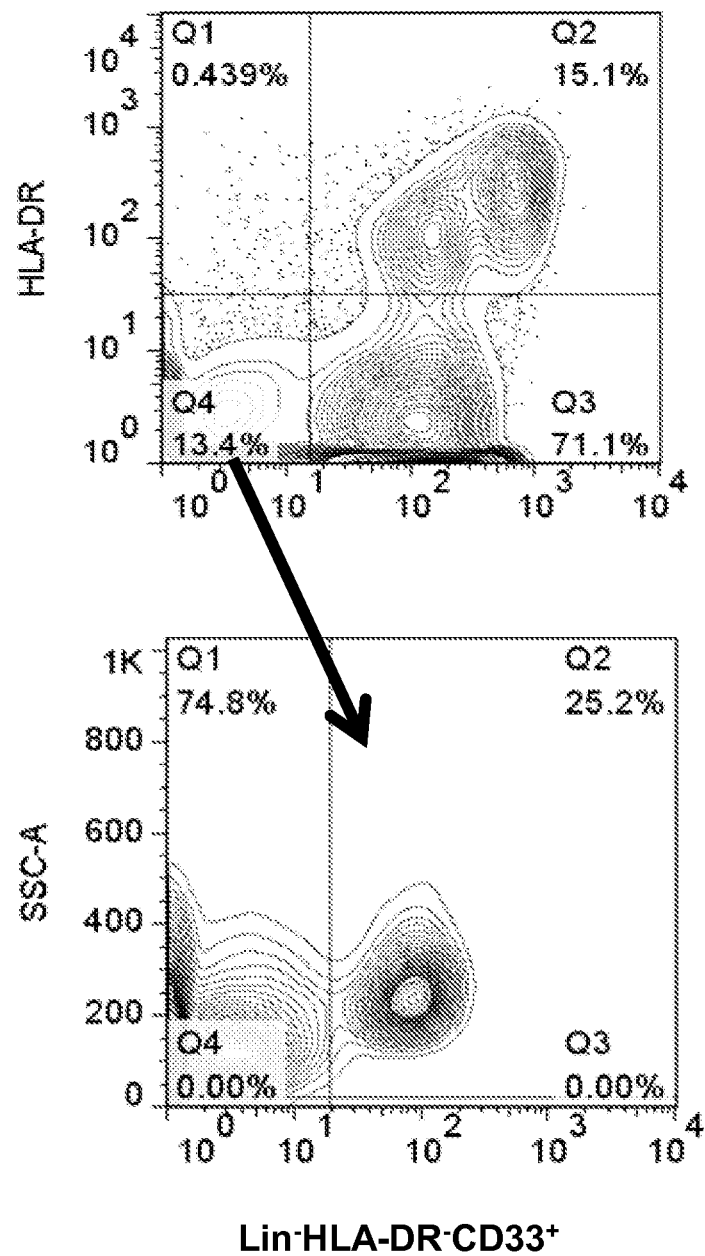
Figure 8B:
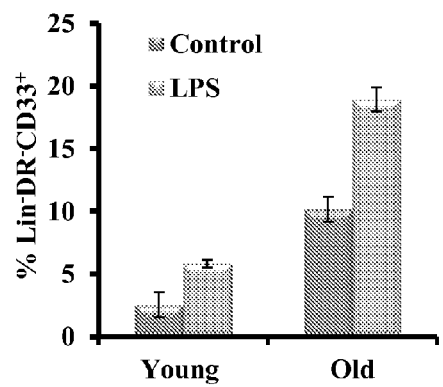
Figure 8C:
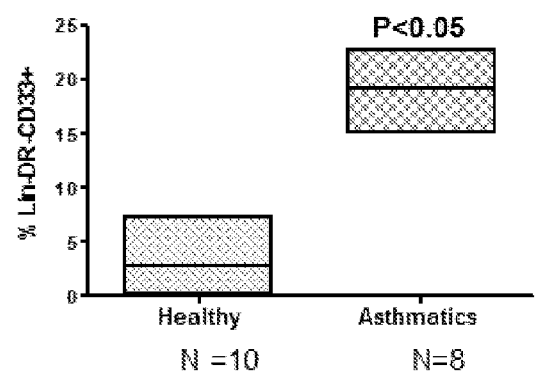
Figure 8D:
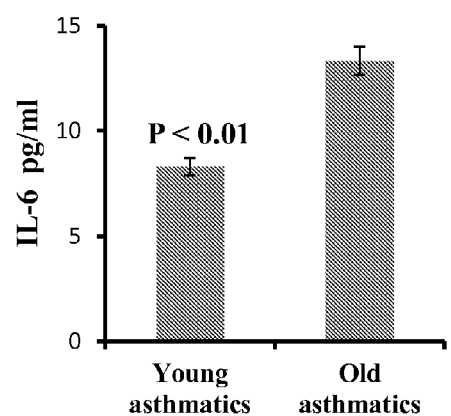
Figure 8E:
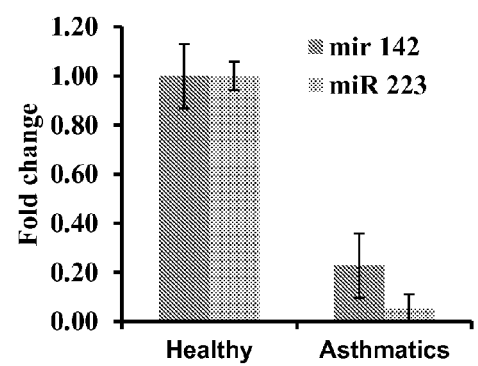

The isolated PBMC were analyzed for the presence of MDSC (Lin$^-$HLADR$^-$CD33$^+$) (FIG. 8A). Both old and asthmatic individuals showed a significant expansion of Lin$^-$HLADR$^-$CD33$^+$ MDSC in their peripheral blood associated with decrease in miR-142/223 levels compared to the healthy and young donors (FIGS. 8B-E). This was associated with decrease in myeloid DCs and plasmacytoid DCs (FIGS. 8F-H).

A small number of inflammatory cytokines was also examined in asthmatics. Among them, an elevated level of IL-6 was significantly associated with old asthmatics (greater than 50 years old) compared to younger asthmatics (less than 50 years old) (data not shown). This finding suggests a possible role of miR-142-MDSC-IL-6 in chronic inflammation in the elderly.

The invention claimed is:

1. A method of modulating differentiation of a myeloid derived suppressor cell (MDSC) comprising: administering an amount of a miR-142 to the MDSC.

2. The method of claim 1, further comprising the step of administering an amount of a miR-223.

3. The method of claim 1, wherein the MDSC differentiates into a macrophage or a dendritic cell.

4. The method of claim 2, wherein the MDSC differentiates into a macrophage or a dendritic cell.

5. The method of claim 2, wherein the miR-142 is administered to the MDSC via a nanoparticle comprising the miR-142.

6. The method of claim 2, wherein the miR-223 is administered to the MDSC via a nanoparticle comprising the miR-223.

7. The method of claim 1, wherein the MDSC is located in a subject.

8. The method of claim 7, wherein the MDSC is located in a spleen.

9. The method of claim 1, wherein the MDSC is removed from a subject prior to the administration and reintroduced into the subject following the administration.

10. The method of claim 9, wherein the MDSC is obtained from the subject in a blood sample or a bone marrow sample.

11. The method of claim 9, wherein the miR-142 is administered to the MDSC via a nanoparticle comprising the miR-142 is administered to the MDSC.

12. A method of modulating differentiation of a group of myeloid derived suppressor cells (MDSCs) comprising administering an amount of a miR-142 in more than one MDSC within the group.

13. The method of claim 12, further comprising the step of administering an amount of a miR-223 in the more than one MDSC.

14. The method of claim 13, wherein the MDSCs differentiate into macrophages or dendritic cells.

15. The method of claim 13, wherein the miR-142 and the miR-223 are administered to the MDSCs via a nanoparticle comprising the miR-142 and the miR-223.

16. The method of claim 15, wherein the MDSCs are located in a subject.

* * * * *

SEQUENCE LISTING

```
<160> NUMBER OF SEQ ID NOS: 2

<210> SEQ ID NO 1
<211> LENGTH: 87
<212> TYPE: DNA
<213> ORGANISM: Homo sapiens
<220> FEATURE:
<221> NAME/KEY: stem_loop
<222> LOCATION: (1)..(87)

<400> SEQUENCE: 1
gacagtgcag tcacccataa agtagaaagc actactaaca gcactggagg gtgtagtgtt      60
tcctacttta tggatgagtg tactgtg                                          87

<210> SEQ ID NO 2
<211> LENGTH: 109
<212> TYPE: DNA
<213> ORGANISM: Homo sapiens
<220> FEATURE:
<221> NAME/KEY: stem_loop
<222> LOCATION: (1)..(109)

<400> SEQUENCE: 2
cctggcctcc tgcagtgcca cgctccgtgt atttgacaag ctgagttgga cactccatgt      60
ggtagagtgt cagtttgtca aatacccaag tgcggcacat gcttaccag               109
```